United States Patent

Lang et al.

[11] 4,445,863
[45] May 1, 1984

[54] ARTIFICIAL TEETH

[76] Inventors: Brien R. Lang, 1415 Folkstone, Ann Arbor, Mich. 48105; Michael E. Razzoog, 6020 Vreland, Ypsilanti, Mich. 48197

[21] Appl. No.: 412,470
[22] Filed: Aug. 30, 1982
[51] Int. Cl.³ .............................................. A61C 13/08
[52] U.S. Cl. .................................................. 433/212
[58] Field of Search ...................... 433/202, 212, 197

[56] References Cited
U.S. PATENT DOCUMENTS 2,473,515 6/1949 Egger .................................... 433/212
2,525,962 10/1950 Silverman ............................. 433/212

Primary Examiner—Robert Peshock
Attorney, Agent, or Firm—Stephenson and Boller; Stephenson and Boller

[57] ABSTRACT

An artificial posterior denture tooth comprising a body shaped to conform generally to the shape of a natural posterior tooth and formed of a plurality of resin materials varying in hardness, wear resistance and strength. The various resins are selectively distributed throughout the body of the tooth to produce an uneven wear pattern consistent with expected changes in the patient's stomatognathic system.

6 Claims, 4 Drawing Figures

ARTIFICIAL TEETH

BACKGROUND AND SUMMARY OF THE INVENTION

This invention relates to artificial denture teeth and in particular to artificial posterior teeth. A principal objective in artificial teeth of this type is to provide a balanced occlusion of opposing maxillary and mandibular teeth. A "balanced occlusion" may be defined as a harmonious relation of the occluding surfaces in centric and eccentric positions within the functional range of the mandible. When a balanced occlusion is achieved, there is simultaneous contact of opposing maxillary and mandibular teeth on both sides of the mouth as the mandible moves within its functional range. This relationship ensures adequate surface area of occlusal contact so as to promote comfort, function and esthetics. In the absence of a balanced occlusion there is a likelihood of deflective occlusal contacts between opposing teeth. Some of the symptoms of this problem include cheek biting, tissue soreness, a lack of chewing efficiency, and unpleasing esthetic effects. Also, this greatly reduces the lateral and horizontal forces applied to the supporting tissues through the denture bases.

The artificial teeth described in the prior art are typically formed of porcelain or plastic. The prior art teeth have been satisfactory from the standpoint of size and shape; in general, it has been possible to closely conform artificial teeth to the sizes and shapes of natural teeth. It has also been possible to achieve a balanced occlusion with the prior art teeth. However, this has required extensive grinding of the teeth to establish the needed tooth contacts for mechanical harmony. Grinding is performed either prior to or following processing of the dentures, and often requires a great deal of effort on the part of the dentist or technician.

The problems of grinding to achieve balanced occlusion are heightened when the oral conditions or "patient factors" of a particular patient do not fit into the circumstances dictated by the design of the denture tooth. Examples of patient factors which normally are not accounted for in the prior art teeth include poor neuromuscular control of jaw movements, discrepancies in the anteroposterior and mediolateral jaw relationships and the need of the patient to look natural and present a pleasant appearance. When patient factors such as these are present, extensive occlusal modification is necessary or balanced occlusion is unattainable. None of the prior art teeth are capable of providing a balanced occlusion universally to every patient without extensive grinding.

Another problem encountered by the prior art teeth is that, even if a balanced occlusion is initially achieved, changes in the patient's stomatognathic system over time can alter tooth contact positions and destroy the balanced relationship. Physiological changes normally occur in the denture supporting tissues as a function of patient aging. As these tissues undergo change, the denture bases assume new positions. This changes the contact relationship of the upper and lower teeth, so that an occlusion that was initially balanced may become deflective. The resulting deflective contacts may accelerate the changes in supporting tissues and may even induce pathological changes in the tissues.

It is an object of the present invention, therefore, to provide an artificial posterior tooth which would permit the formation of a balanced occlusion without extensive grinding. Another object is to provide an artificial posterior tooth which would permit the formation of balanced occlusion in all patients, regardless of variations in individual patient factors, without extensive grinding. Still, another object is to provide an artifical posterior tooth which is adaptable over time to changes in the patient's stomatognathic system to ensure a continuously balanced occlusion.

The artificial posterior tooth of the present invention consists of a body formed of a plurality of resin materials varying in hardness, wear resistance, and strength. The body is shaped to conform generally to the shape of a natural tooth. The resin materials are selectively distributed throughout the tooth body to produce an uneven wear pattern which is consistent with the changes expected in the individual patient's stomatognathic system.

In a preferred embodiment of a denture system produced according to this invention, each pair of opposing maxillary and mandibular teeth is constructed of three resins. A first resin is used to form the lingual cusp(s) (a premolar has a single lingual cusp, while a molar has two, known as the mesiolingual and distolingual cusps) and an adjacent portion of the buccal cusp(s) of the maxillary tooth. A second resin is used to form the remainder of the maxillary tooth. The second resin is also used to form the lingual cusp(s) and an adjacent portion of the buccal cusp(s) of the mandibular tooth. A third resin is used to form the remainder of the mandibular tooth. The first resin has strength, wear resistance, and hardness characteristics which are greater than those of the second resin, which in turn has greater strength, wear resistance, and hardness than the third resin. Examples of resins having acceptable characteristics include the following:

Filled and unfilled dental resins which contain up to 80% of the inorganic fillers, for example, glass beads, rods, quartz, or lithium aluminum silicate. The particular filler or fillers used will determine the hardness of the finished resin. The filler particles are coated with a coupling agent, such as an appropriate silicone, to provide an adhesive bond between the filler and the resin. The matrix resin is a reaction product of the epoxy resin (glycidye acrylate). The reaction product is thinned with methyl methacrylate or some other comonomer of low viscosity.

In the embodiment described above, the areas of wear will be the occluding surfaces of the mandibular tooth (resins #2 and 3) as it wears against the maxillary occluding surface (resin #1) in various jaw movements. The least wear will occur in the area of greatest contact, that is, where the maxillary lingual cusp (resin #1) contacts the opposing occlusal surface of the mandibular tooth (resin #2). Thus, wear will occur where it is needed to prevent development of deflective contacts but not where it would detract from mechanical effectiveness.

It is to be understood that the resins listed above are for illustrative purposes only, and the invention is not limited to these resins or to the embodiment described above. Whichever resins are employed may be selectively distributed throughout the tooth body in any manner which will achieve the selective wear characteristics necessary to ensure a continuously balanced occlusion.

The invention thus provides an artificial posterior tooth with selective wear characteristics which inhibit the development of deflective occlusal contacts and promote the development of a balanced occlusion. The tooth can therefore be used to achieve a balanced occlusion for all patients, regardless of individual oral conditions. The distribution and composition of the resins can be varied from patient to patient to produce a wear pattern that ensures balanced occlusion despite temporal physiological changes in the individual patient's stomatognathic system. Thus, the tooth of this invention enables a more esthetically pleasing appearance, functions more harmoniously and is more comfortable and physiologically beneficial than teeth described in the prior art.

DETAILED DESCRIPTION OF THE PREFERRED EMBODIMENT

Figure 1:
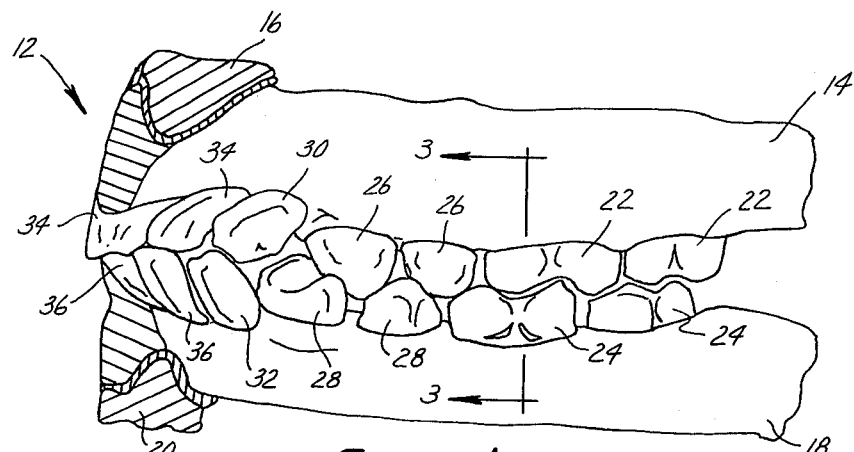
FIG. 1 is a lingual sectional view of a denture and teeth supported thereon.

With reference to the drawing, the present invention relates to an artificial posterior tooth of improved construction, indicated generally at 10, and an improved denture, indicated generally at 12, which incorporates teeth 10 of improved construction. As seen in FIG. 1, the denture 12 comprises an upper denture base member 14 which is adapted to fit onto the patient's maxillary residual ridge 16, a lower denture base member 18 adapted to fit onto the patient's mandible or lower residual ridge 20, and a complete set of artificial teeth, including posterior teeth identified generally by the number 10, supported on the denture base members 14 and 18.

A complete set of teeth includes "posterior" teeth, namely, molars and premolars indicated by the numerals 22, 24, 26, and 28. More particularly, the molars and premolars are identified as maxillary molars 22 (2 on each side), mandibular molars 24 (2 on each side), maxillary premolars 26 (2 on each side) and mandibular premolars 28 (2 on each side). A complete set of teeth also includes maxillary canines 30 (1 on each side), mandibular canines 32 (1 on each side), maxillary incisors 34 (2 on each side), and mandibular incisors 36 (2 on each side).

Figure 2:
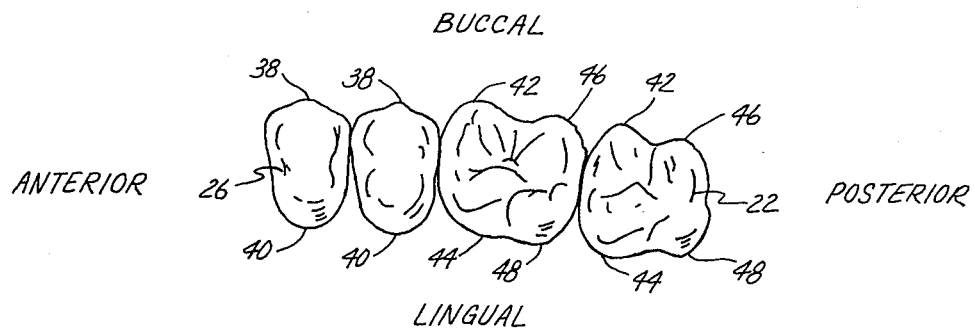
FIG. 2 is an occlusal view of a set of maxillary posterior teeth.

As seen in FIG. 2, each of the maxillary premolars has a buccal cusp 38 and a lingual cusp 40. Each of the maxillary molars has two buccal cusps and two lingual cusps: a mesiobuccal cusp 42, a mesiolingual cusp 44, a distobuccal cusp 46, and a distolingual cusp 48.

Figure 2A:
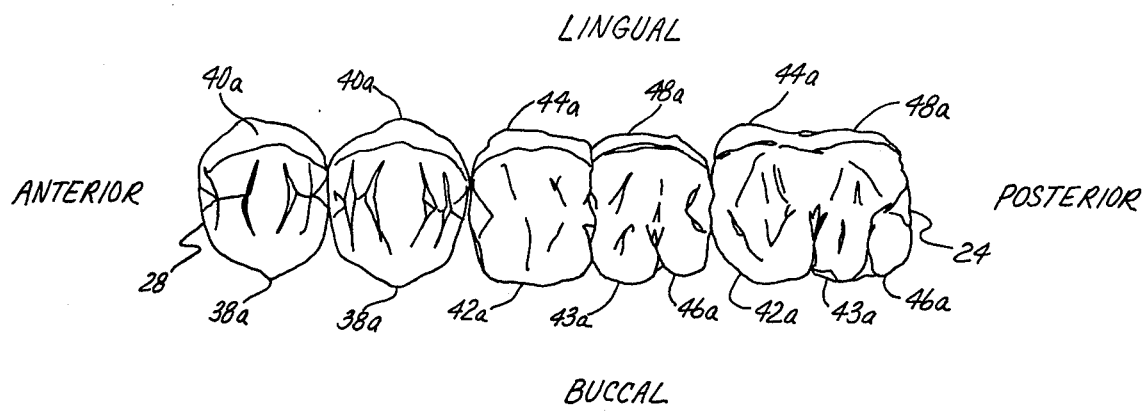
FIG. 2a is an occlusal view of a set of mandibular posterior teeth.

As seen in FIG. 2a, each of the mandibular premolars has a buccal cusp 38a, and a lingual cusp 40a. Each of the mandibular molars has three buccal cusps and two lingual cusps: a mesiobuccal cusp 42a, a buccal cusp 43a, a distobuccal cusp 46a, and a mesiolingual cusp 44a, and a distolingual cusp 48a.

Figure 3:
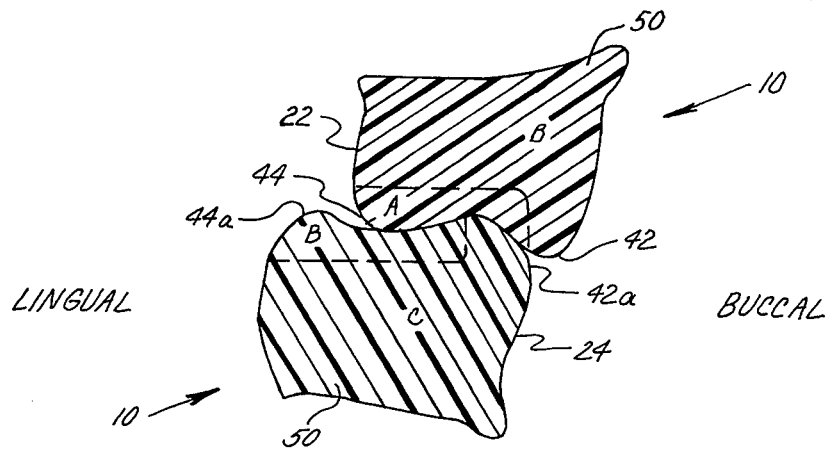
FIG. 3 is a bucco-lingual view of a preferred embodiment of a pair of opposing maxillary and mandibular posterior teeth constructed according to the present invention, as seen from substantially the line 3—3 in FIG. 1 on an enlarged scale.

As seen in FIG. 3, each of the artificial posterior teeth 10 of this invention consists of a body 50 formed of a plurality of resins of varying hardness, wear resistance, and strength selectively distributed throughout the body 50. The body 50 is shaped to conform generally to the shape of a natural tooth. FIG. 3 shows a preferred embodiment of a pair of opposing teeth 10 in occlusion. For the purpose of illustration it will be assumed that the upper tooth 10 is a maxillary first molar 22 and the lower tooth is the mandibular first molar 24, although the teeth 10 shown in FIG. 3 could be any set of occluding posterior teeth.

In the embodiment of FIG. 3, the resins forming the bodies 50 of the teeth 10 are distributed according to the broken lines. Thus, a first resin is used to form the cusp portion designated by the letter "A", which is the lingual cusp(s) (44, 48), and an adjacent portion of the buccal cusp(s) (42, 46) of the maxillary molar 22. A second resin is used to form the portions designated by the letter "B", which include the remainder of the maxillary molar 22 and the lingual cusp(s) (44a, 48a) and an adjacent portion of the buccal cusp(s) (42a, 43a, 46a) of the mandibular molar 24. A third resin is used to form the area designated by the letter "C", which is the remainder of the mandibular molar 24. According to this embodiment, the first resin "A" is more resistant to wear that the second resin "B", which in turn is more wear resistant than the third resin "C". This distribution of resins produces wear patterns in which the areas most subject to wear, are also the areas most susceptible to the formation of deflective occlusal contacts. The illustrated embodiment functions to inhibit the formation of these deflective occlusal contacts.

The invention thus provides an improved artificial tooth 10 and denture 12 which inhibit the forming of deflective contacts and promote a continuously balanced occlusion. The distribution of resins throughout the tooth body 50 produces a selective wear pattern that can be adapted to the individual characteristics of various patients. The resulting wear pattern also makes the tooth 10 adaptable to temporal changes in an individual patient's stomatognathic system so that the balanced occlusion is self-perpetuating.

What is claimed is:

1. An artificial posterior denture tooth comprising a body shaped to conform generally to the shape of a natural posterior tooth and having wear surfaces, said body being formed of a plurality of resin materials varying in hardness, wear resistance, and strength, said resin materials being selectively distributed throughout said body to produce an uneven wear pattern on at least some of said surfaces.

2. The artificial posterior tooth according to claim 1 wherein the body of said tooth includes buccal and lingual cusps, and the resin of which said lingual cusp(s) is formed has greater strength, wear resistance and hardness than the resins of which the rest of said tooth body are formed.

3. A denture comprising upper and lower denture base members adapted to fit onto the patient's upper and lower residual ridges and a complete set of teeth including posterior teeth supported on said denture base members and shaped to conform generally to the shape of natural teeth, each of said posterior teeth comprising a body having wear surfaces and formed of a plurality of resin materials varying in hardness, wear resistance and strength selectively distributed throughout said body to produce an uneven wear pattern on at least some of said surfaces consistent with expected changes in the stomatognathic system.

4. The denture according to claim 3 wherein each of said posterior teeth includes lingual and buccal cusps and the lingual cusp(s) of each maxillary posterior tooth is formed of a resin with greater hardness, wear resistance, and strength characteristics than the resin used to form the occluding surfaces of the opposing mandibular tooth.

5. The denture according to claim 4 wherein, in each opposing pair of occluding maxillary and mandibular posterior teeth, the lingual cusp and an adjacent portion of the buccal cusp of the maxillary tooth are formed of a first resin, the remainder of the maxillary tooth and the lingual cusp and an adjacent portion of the buccal cusp of the opposing mandibular tooth are formed of a second resin and the remainder of the mandibular tooth is formed of a third resin.

6. The denture according to claim 5 wherein said first resin has greater hardness, wear resistance, and strength characteristics than said second resin and said second resin has greater hardness, wear resistance and strength characteristics than said third resin.

* * * * *